United States Patent [19]

Gremmelmaier et al.

[11] 4,205,167

[45] May 27, 1980

[54] PROCESS FOR PRODUCING CYAMELURIC CHLORIDE

[75] Inventors: Claude Gremmelmaier, Aesch; Jean Riethmann, Rheinfelden, both of Switzerland

[73] Assignee: Ciba-Geigy Corporation, Ardsley, N.Y.

[21] Appl. No.: 26,262

[22] Filed: Apr. 2, 1979

[51] Int. Cl.$^2$ .......................................... C07D 403/14
[52] U.S. Cl. .................................................. 544/209
[58] Field of Search ....................... 544/204, 209, 190

[56] References Cited

PUBLICATIONS

Redemann et al., *Jour. Amer. Chem. Soc.*, vol. 62, pp. 842–846 (1940).

*Primary Examiner*—John M. Ford
*Attorney, Agent, or Firm*—Harry Falber

[57] ABSTRACT

A process for the production of cyameluric chloride is disclosed which comprises passing cyanuric chloride, mixtures of cyanuric chloride and cyanogen chloride, or cyanogen chloride, at temperatures of 200° to 700° C., together with oxygen over active charcoal, and separating the resulting cyameluric chloride by desublimation from the gas mixture obtained.

Cyameluric chloride is a valuable intermediate.

6 Claims, No Drawings

PROCESS FOR PRODUCING CYAMELURIC CHLORIDE

The present invention relates to a process for producing cyameluric chloride.

2,5,8-Trichlorotri-s-triazine of the formula

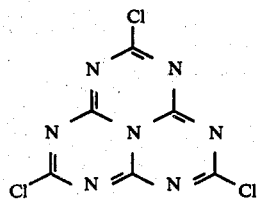

is designated as cyameluric chloride. Cyameluric chloride is a valuable intermediate for producing various products, such as gelling agents for aliphatic hyrocarbons (see U.S. Pat. No. 3,089,875), fluorine-containing oxidants which can be used as additives for rocket propellants (see U.S. Pat. No. 3,202,659), stabilisers for photographic emulsions (see U.S. Pat. Nos. 2,704,716 and 2,801,172), and dyes (see German Pat. No. 1,102,321).

The producing of cyameluric chloride by reaction of cyameluric acid or an alkali cyamelurate with phosphorus pentachloride in a closed system is known (see J. Amer. Soc., 62, 842 (1940)). This reaction can be performed either in a bomb tube at 230° C. (see J. Org. Chem. 27, 4264 (1962)) or in a suitable inert solvent, for example o-dichlorobenzene (see German Pat. specification No. 1,102,321). The cyameluric acid or alkali cyamelurate, required as starting material, can for its part be produced by alkaline saponification of melon, a process wherein there is firstly obtained the alkali salt of the cyameluric acid, from the aqueous solution of which can be separated, by the addition of hydrochloric acid, the cyameluric acid (see J. Amer. Chem. Soc. 61, 3420 (1939) and Liebigs Anm. Chem. 73, 228 (1855)). Finally, the melon required for producing cyameluric acid can be produced by pyrolysis of melamine at 500° C. (see J. Appl. Chem. 9, 340 (1959)), by slow heating of ammonium thiocyanate (see Z. Angew. Chem. 39, 1071 (1926)), or by pyrolysis of pseudothiocyanogen which, for its part, is obtained by chlorination of sodium thiocyanate in aqueous solution (see J. Amer. Chem. Soc. 61, 3420 (1939)).

The application of the aforementioned processes for producing cyameluric chloride leads in each case to a multistage process, the individual stages of which are in part difficult to carry out and difficult to control. Apart from these technical difficulties, a further disadvantage associated with the application of the aforesaid processes is that, in consequence of numerous secondary reactions, cyameluric chloride is obtained only in low yields and in an impure form. The processes mentioned above are therefore unsuitable for commercial production of cyameluric chloride.

It is therefore the object of the present invention to suggest a process which renders possible the production of pure cyameluric chloride in a simple manner.

It has been found that very pure cyameluric chloride is formed when cyanuric chloride, mixtures of cyanuric chloride and cyanogen chloride, or cyanogen chloride are passed, at temperatures of 200° to 700° C., together with oxygen, over active charcoal. The process according to the invention for producing cyameluric chloride comprises passing cyanuric chloride, mixtures of cyanuric chloride and cyanogen chloride, or cyanogen chloride, at a temperature of 200° to 700° C., together with oxygen over active charcoal, and separating the resulting cyameluric chloride by desublimation from the gas mixture obtained.

The active charcoal used can advantageously be the active charcoal customarily employed for producing cyanuric chloride. Cyanuric chloride is primarily used as starting material for the process according to the invention. Since however cyanuric chloride under the applied reaction conditions on active charcoal is partially split back to form cyanogen chloride, it is also possible to use mixtures of cyanuric chloride and cyanogen chloride in the reaction. And since moreover under the reaction conditions cyanuric chloride is formed from cyanogen chloride, it is also possible to use pure cyanogen chloride as starting material.

Within the given temperature range of 200° to 700° C., temperatures of 300° to 450° C. are preferred. The contact times and the quanitity proportions of the reactants are not critical and can be varied within wide limits. It is merely necessary that a small amount of oxygen be fed in simultaneously with the reaction mixture. The oxygen can be supplied in the pure form, in the form of air or in the form of other oxygen-containing or oxygen-yielding gases. The oxygen is preferably supplied in the form of air. On account of its low vapour pressure, the formed cyameluric chloride can be separated in pure form from the reaction mixture in a simple manner by desublimation. This desublimation is performed advantageously at a temperature of 200° to 250° C., preferably at 200° to 220° C. The residual gas containing cyanuric chloride and cyanogen chloride can be fed back, optionally after the addition of fresh oxygen, to the reaction vessel. In some cases, especially where the oxygen is supplied in the form of air, it is however advantageous to further process the residual gas. This can be effected for example by cooling the residual gas to room temperature to obtain the quantitative separation of the cyanuric chloride. From the residual gas obtained after separation of the cyanuric chloride, it is then possible to isolate the cyanogen chloride either by condensation or by absorption with a suitable solvent, for example carbon tetrachloride. The cyanuric chloride and cyanogen chloride recovered in this manner can subsequently be passed, together with fresh oxygen, again over the active charcoal contact.

Starting with cheap, readily accessible raw materials, it is possible by the process according to the invention to produce very pure cyameluric chloride in good yield. A further advantage of the process according to the invention is that the cyameluric chloride can be produced with a high space-time yield. A certain disadvantage of the process is merely that the conversion to cyameluric chloride is low. This can however easily be offset by feeding back the residual gas obtained after separation of the cyameluric chloride, or the unreacted cyanuric chloride and cyanogen chloride contained in this residual gas, to the reaction vessel.

The process according to the invention is further illustrated by the Examples which follow.

EXAMPLE 1

A vertically arranged, electrically heated pyrex glass tube with an inside diameter of 28 mm and a length of 500 mm and containing a concentric tube of 5 mm diameter, in which thermocouples are fixed at various heights, serves as the reactor. At the lower end of the reactor is located a receiver which is used for desublimating the cyameluric chloride and which can be thermostatically controlled at a temperature of 200° C. After this receiver is inserted a second receiver in which the residual gas is cooled to room temperature to effect separation of the cyanuric chloride. The receiver for separating cyanuric chloride is connected to an exhaust-gas pipe which is provided with devices for sampling and which has an absorption column filled with aqueous sodium hydroxide solution.

The reactor is charged with 20 g (45 ml) of a commercial coarse-grained active charcoal having a specific surface area (BET) of 1100 m²/g. Whilst being flushed with air (0.5 l/min.), the reactor is heated to 400° C. and is held for one hour at this temperature. There are subsequently continuously passed 1.16 kg/h of cyanuric chloride vapour and 30 l/h of air at 400° C. over the catalyst. After 370 operating hours, 1.108 kg of cyameluric chloride has been precipitated in the first receiver thermostatically controlled at 200° C. The purity of the product on the basis of the chlorine determination according to Wurzschmitt is 99.5 to 100% and on the basis of the nitrogen determination according to Kjeldahl 98.6 to 100%.

The space-time yield is 66.5 g of cyameluric chloride per liter of catalyst and hour.

The effective consumption of cyanuric chloride, ascertained from the difference between supplied cyanuric chloride and recovered cyanuric chloride, is 3.50 kg, which corresponds to a yield of 31.7 percent by weight.

The analysis of the uncondensed gases and of the wash liquor shows that these gases contain, in addition to phosgene, chlorine, carbon dioxide and small amounts of carbon monoxide, dinitrogen monoxide and carbon tetrachloride, also 1.48 kg of cyanogen chloride. There follows from this, taking into account the fact that 7 mols of cyanogen chloride or 7/3 mols of cyanuric chloride are required for 1 mol of cyameluric chloride, that there is a selectivity of cyameluric chloride formation of 85%.

EXAMPLE 2

Cyanuric chloride/air mixtures of varying composition are reacted under different reaction conditions in the reactor described in Example 1. The test results are summarised in the following Table.

| Test | Temperature [°C.] | Cyanuric chloride [kg/h] | Air [l/h] | Molar ratio air/cyanuric chloride | Space-time yield [g of cyameluric chloride / l of catalyst · hour] |
|---|---|---|---|---|---|
| 1 | 300 | 0,115 | 12 | 0,86 | 0,5 |
| 2 | 400 | 2,32 | 60 | 0,21 | 82,1 |
| 3 | 400 | 1,16 | 30 | 0,21 | 68,4 |
| 4 | 400 | 0,23 | 6 | 0,21 | 15,1 |
| 5 | 400 | 0,115 | 3 | 0,21 | 17,6 |
| 6 | 400 | 0,058 | 1,5 | 0,21 | 6,5 |
| 7 | 400 | 0,029 | 0,75 | 0,21 | 4,1 |
| 8 | 400 | 0,23 | 1,12 | 0,04 | 17,0 |
| 9 | 400 | 0,23 | 24 | 0,80 | 16,7 |
| 10 | 400 | 0,029 | 12 | 3,41 | 2,1 |
| 11 | 430 | 0,115 | 3 | 0,21 | 31,3 |
| 12 | 450 | 0,115 | 3 | 0,21 | 37,8 |
| 13 | 500 | 0,115 | 3 | 0,21 | 36,2 |
| 14 | 500 | 0,58 | 15 | 0,21 | 105,4 |
| 15 | 400 | 1,16 | 30* | — | 0 |

*nitrogen in place of air

The test results show that the amount of air has only a slight effect on the formation of cyameluric chloride. Test 15 shows however that definitely oxygen has to be present for the formation of cyameluric chloride. The formation of cyameluric chloride increases with the increase of the cyanuric chloride throughput and of the temperature. The selectivity of the reaction slowly decreases however at temperatures above 430° C. Moreover, at these temperatures the active charcoal is slowly oxidised to carbon dioxide.

EXAMPLE 3

The reactor described in Example 1 is charged with 50 g of active charcoal, and is heated as in Example 1 to 400° C. There are then passed through the reactor at 400° C. 0.06 kg/h of cyanogen chloride and 1.2 l/h of air. The amount of cyameluric chloride formed is 0.7 g/h.

What is claimed is:

1. A process for producing cyameluric chloride, which process comprises passing cyanuric chloride, mixtures of cyanuric chloride and cyanogen chloride, or cyanogen chloride, at temperatures of 200° to 700° C., together with oxygen over active charcoal, and separating the resulting cyameluric chloride by desublimation from the gas mixture obtained.

2. A process according to claim 1, wherein cyanuric chloride is passed at a temperature of 200° to 700° C. together with oxygen over active charcoal.

3. A process according to claim 1, wherein the reaction is performed at a temperature of 200° to 450° C.

4. A process according to claim 1, wherein the desublimation of the cyameluric chloride is performed at a temperature of 200° to 250° C.

5. A process according to claim 1, wherein the desublimation of the cyameluric chloride is performed at a temperature of 200° to 220° C.

6. A process according to claim 1, wherein the residual gas containing the cyanuric chloride and cyanogen chloride is fed back to the reactor.

* * * * *